United States Patent
Heinz

(10) Patent No.: US 8,366,776 B2
(45) Date of Patent: Feb. 5, 2013

(54) VERTEBRAL IMPLANTS HAVING PREDETERMINED ANGULAR CORRECTION AND METHOD OF USE

(75) Inventor: Eric S. Heinz, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1016 days.

(21) Appl. No.: 11/403,351

(22) Filed: Apr. 13, 2006

(65) Prior Publication Data

US 2007/0270957 A1 Nov. 22, 2007

(51) Int. Cl.
*A61F 2/44* (2006.01)

(52) U.S. Cl. .................................. 623/17.16

(58) Field of Classification Search ............... 606/249, 606/248; 623/17.11–17.16
See application file for complete search history.

(56) References Cited

U.S. PATENT DOCUMENTS

| | | | |
|---|---|---|---|
| 4,304,011 A | 12/1981 | Whelan, III | |
| 4,997,432 A | 3/1991 | Keller | |
| 5,192,327 A * | 3/1993 | Brantigan | 623/17.11 |
| 5,609,637 A | 3/1997 | Biedermann et al. | |
| 6,106,557 A | 8/2000 | Robioneck et al. | |
| 6,146,421 A | 11/2000 | Gordon et al. | |
| 6,159,211 A * | 12/2000 | Boriani et al. | 606/279 |
| 6,432,106 B1 | 8/2002 | Fraser | |
| 6,447,548 B1 | 9/2002 | Ralph et al. | |
| 6,468,311 B2 | 10/2002 | Boyd et al. | |
| 6,554,863 B2 | 4/2003 | Paul et al. | |
| 6,676,703 B2 | 1/2004 | Biscup | |
| 6,682,564 B1 | 1/2004 | Duarte | |
| 6,719,794 B2 * | 4/2004 | Gerber et al. | 623/17.11 |
| 6,830,589 B2 | 12/2004 | Erickson | |
| 7,704,280 B2 * | 4/2010 | Lechmann et al. | 623/17.15 |
| 2002/0082701 A1 * | 6/2002 | Zdeblick et al. | 623/17.16 |
| 2003/0191531 A1 * | 10/2003 | Berry et al. | 623/17.11 |
| 2003/0199980 A1 * | 10/2003 | Siedler | 623/17.11 |
| 2004/0049272 A1 | 3/2004 | Reiley | |
| 2004/0122518 A1 | 6/2004 | Rhoda | |
| 2004/0133279 A1 | 7/2004 | Krueger et al. | |
| 2004/0176843 A1 * | 9/2004 | Zubok et al. | 623/17.14 |
| 2005/0187632 A1 * | 8/2005 | Zubok et al. | 623/17.14 |

(Continued)

FOREIGN PATENT DOCUMENTS

WO 2007/087562 8/2007

OTHER PUBLICATIONS

"International Search Report," International Application No. PCT/US2007/065960, Sep. 19, 2007, European Patent Office, Rijswijk, Netherlands.

*Primary Examiner* — Ellen C Hammond
*Assistant Examiner* — Atiya Mahmud

(57) ABSTRACT

A vertebral implant for use in establishing desired spinal curvatures includes separate implant bodies. Each body may include an associated angle between inferior and superior surfaces of the body. Further, the implant bodies may be stacked so that the associated angles are oriented in different anatomical planes. The implant bodies may be secured to one another with a connector. The implant bodies may be used either independently or in conjunction with one another to achieve a desired spinal curvature. Each implant body may include bone engagement features that extend outward from the superior and inferior surfaces of the implant body. The implant bodies may include recesses that are positioned to correspond to the bone engagement protrusions in other implant bodies to allow contact between the inferior and superior surfaces of the respective implant bodies.

10 Claims, 12 Drawing Sheets

U.S. PATENT DOCUMENTS

| | | |
|---|---|---|
| 2005/0277919 A1 | 12/2005 | Slivka et al. |
| 2006/0009850 A1* | 1/2006 | Frigg et al. ................ 623/17.13 |
| 2006/0015184 A1 | 1/2006 | Winterbottom et al. |
| 2006/0190082 A1* | 8/2006 | Keller et al. ............... 623/17.11 |
| 2006/0212118 A1* | 9/2006 | Abernathie ................ 623/17.11 |
| 2008/0133013 A1* | 6/2008 | Duggal et al. ............. 623/17.16 |

* cited by examiner

# VERTEBRAL IMPLANTS HAVING PREDETERMINED ANGULAR CORRECTION AND METHOD OF USE

BACKGROUND

The human spine serves many functions. The vertebral members of the spinal column protect the spinal cord. Furthermore, moveable facet joints and resilient discs disposed between the vertebral members permit motion between individual vertebral members. The spinal column also supports other portions of the human body. When viewed from a posterior or anterior direction, the vertebral members are generally aligned, although the width of the vertebral members generally increases from the cervical region to the lumbar region. However, when viewed from a lateral direction, the spine is curved to absorb loads and maintain the balance of the upper body. Abnormal curvatures may occur in some patients. For example, kyphosis may describe an exaggerated posterior curvature in the thoracic region. Lordosis may describe an exaggerated anterior curvature of the lumbar region. Scoliosis may describe an abnormal lateral curvature.

The composite sum of the angular relation between adjacent vertebral members makes up the overall curvature of the spine. Thus, one technique to correct abnormal spinal curvatures is to insert interbody implants that include a desired correction angle between vertebral bodies in the spine. The correction angle may be in the coronal plane or the sagittal plane. It is certainly possible to include implants that provide both coronal and sagittal correction of multiplanar defects. For example, a single interbody implant may provide a desired angular correction in the coronal plane and a separate desired angular correction in the sagittal plane. An implant with this configuration provides a compound correction that is the vector combination of the two corrections. A full set of implants may be provided that account for all possible corrections in both coronal and sagittal planes. However, when one considers the number of correction angles that are possible in both directions, it becomes impractical to manufacture, stock, and have available all of the possible combinations for implantation into a patient. Furthermore, implants that provide correction in both coronal and sagittal planes provide a unique combination of correction angles that are likely unusable in most cases.

SUMMARY

Illustrative embodiments disclosed herein are directed to a vertebral implant for use in establishing desired spinal curvatures. The vertebral implant may include separate implant bodies. Each body may include an associated angle between inferior and superior surfaces of the implant body. Further, the implant bodies may be stacked so that the associated angles are oriented in different anatomical planes. For example, the associated angle in one body may correspond to a coronal plane in a patient while the associated angle in another body may correspond to a sagittal plane in a patient.

The implant bodies may be secured to one another with a connector. The implant bodies may be used either independently or in conjunction with one another to achieve a desired spinal curvature. Each implant body may include bone engagement features that extend outward from the superior and inferior surfaces of the implant body. The implant bodies may include recesses that are positioned to correspond to the bone engagement protrusions in the other implant bodies to allow contact between the inferior and superior surfaces of the respective implant bodies.

DETAILED DESCRIPTION

Figure 1:
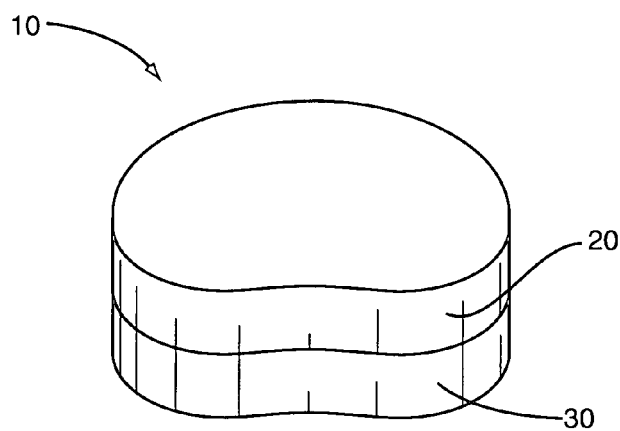
FIG. 1 is a perspective view of a vertebral implant according to one embodiment.

The various embodiments disclosed herein relate to a vertebral implant in which interchangeable sets of coronal angle implants and sagittal angle implants may be used either independently or in conjunction with one another to achieve a desired angle of spinal correction. Reference number 10 in FIG. 1 generally identifies one example of an implant with a coronal angle implant 20 in a stacked configuration with a sagittal angle implant 30. The representative vertebral implant 10 is illustrated as a disc replacement implant that is inserted between vertebral bodies of a patient as part of a disc replacement surgery. In addition, the vertebral implant 10 may include a height sufficient to replace one or more vertebral levels as part of a vertebrectomy or corpectomy surgery. The vertebral implant 10 is illustrated with the coronal angle implant 20 disposed superior to the sagittal angle implant 30, though it should be understood that the opposite relationship may be used as desired.

The vertebral implant 10, including the coronal angle implant 20 and sagittal angle implant 30 may be constructed from biocompatible metal alloys such as titanium, cobalt-chrome, and stainless steel. The vertebral implant 10 may be constructed from non-metallic materials, including for example, ceramics, resins, or polymers, such as UHMWPE and implantable grade polyetheretherketone (PEEK) or other similar materials (e.g., PAEK, PEKK, and PEK). The vertebral implant 10 may be constructed of synthetic or natural bone or bone composites. The coronal angle implant 20 and sagittal angle implant 30 may be constructed of the same or different materials. For example, the coronal angle implant 20 may include a different modulus of elasticity than the sagittal angle implant 30 to provide more or less resistance to motion in a given plane. Furthermore, coronal angle implant 20 and the sagittal angle implant 30 may include the same or different heights. Those skilled in the art will comprehend a variety of material choices that are suitable for the illustrated vertebral implant 10.

Figure 2:
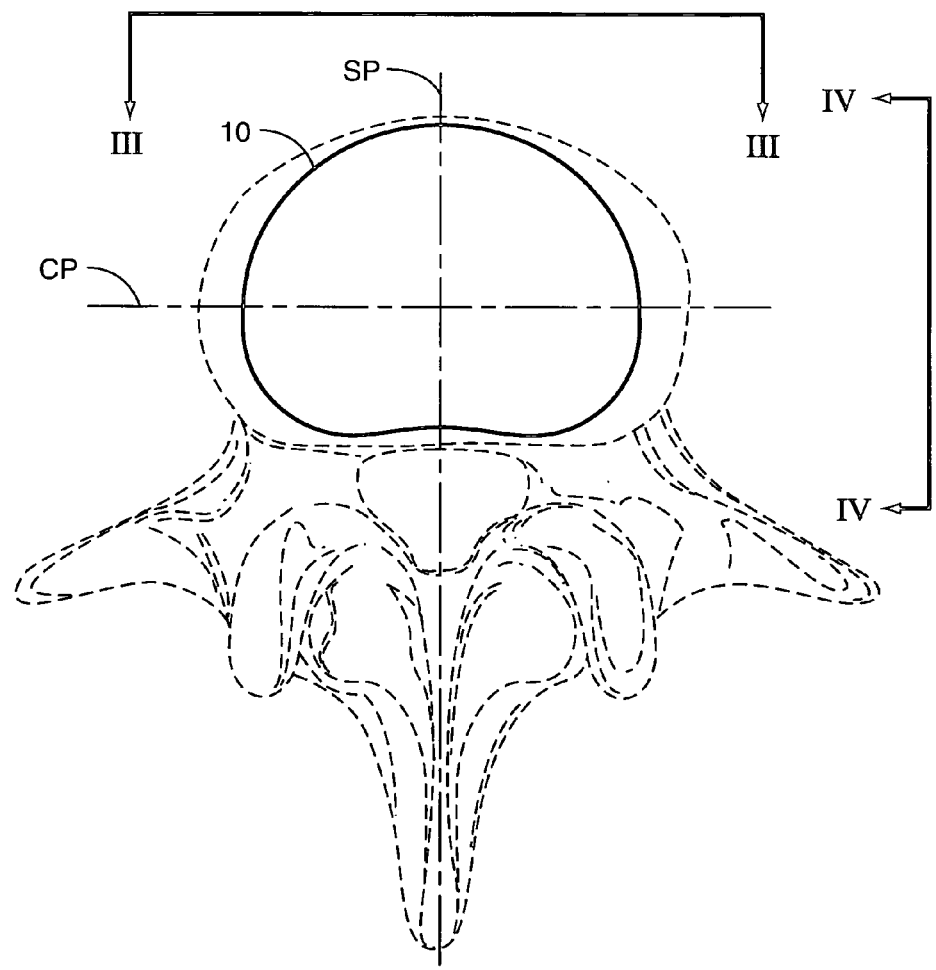
FIG. 2 is a top view of a vertebral implant according to one embodiment shown relative to a vertebral body.
Figure 3:
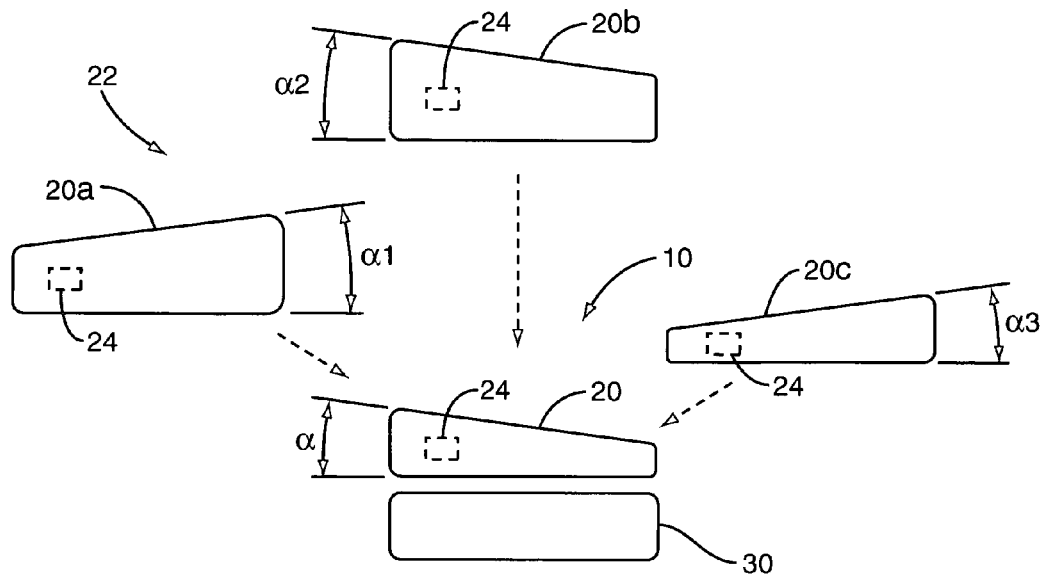
FIG. 3 is an anterior view of a vertebral implant illustrating a set of different coronal angle implants according to one embodiment.
Figure 4:
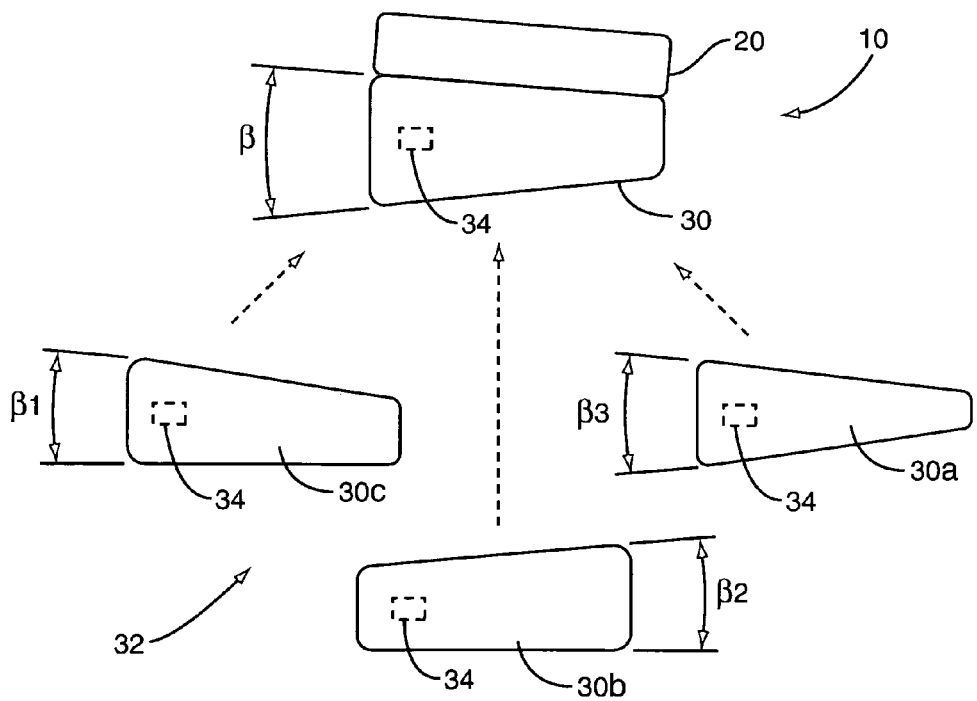
FIG. 4 is a lateral view of a vertebral implant illustrating a set of different sagittal angle implants according to one embodiment.

As suggested above, the exemplary vertebral implant 10 may be inserted between vertebral bodies in the region normally occupied by an interbody disc. FIG. 2 illustrates the vertebral implant 10 in position relative to a dashed line representation of a vertebral body V. FIG. 2 also illustrates a sagittal reference plane SP and a coronal reference plane CP. As shown, the sagittal plane SP is the imaginary anatomical plane that bilaterally separates the body into left and right halves. The coronal plane CP is the imaginary anatomical plane that separates the body into anterior and posterior regions. FIGS. 3 and 4 illustrate anterior and lateral views of the exemplary vertebral implant 10 according to the view lines shown in FIG. 2. Specifically, FIG. 3 is shown from a direction substantially normal to the coronal plane while FIG. 4 is shown from a direction substantially normal to the sagittal plane.

FIGS. 3 and 4 show that the coronal angle implant 20 and the sagittal angle implant 30 are substantially tapered or wedge-shaped in a particular direction. FIG. 3 depicts a coronal angle α associated with the coronal angle implant 20. By comparison, the sagittal angle implant 30 does not include any significant angle or tilt in the coronal plane. In other words, selecting an appropriate coronal angle implant 20, independent of the selected sagittal angle implant 30, may provide a desired coronal angle correction α. To that end, FIG. 3 also shows various alternative coronal angle implants 20a-c that may be used in lieu of coronal angle implant 20 if different coronal angles, α1, α2, or α3 are desired. Together, the coronal angle implants 20, 20a-c may form part of a set 22 of coronal angle implants that comprises individual implants that include different coronal angles. The set 22 may include individual implants that include different heights as well. As a non-limiting example, the set 22 may include a plurality of different implants, each including a different coronal angle α varying from about −20 degrees to about +20 degrees. Furthermore, each coronal angle implant 20, 20a-c may include a designator 24 to distinguish the individual implant 20, 20a-c from others in the set 22. In one embodiment, the designator 24 may include a graphical marking indicating the coronal angle in degrees. In one embodiment, the designator 24 may include an alphanumeric identifier representing one of a sequence of characters. In one embodiment, the designator 24 may include a color code. In each case, the designator 24 may be engraved, etched, printed, marked, adhered, or otherwise displayed on the coronal angle implant 20, 20a-c or on packaging associated with the implant. Other possible designators 24 may be used as well.

FIG. 4 depicts a sagittal angle β associated with the sagittal angle implant 30. By comparison, the coronal angle implant 20 does not include any significant angle or tilt in the sagittal plane. In other words, selecting an appropriate sagittal angle implant 30, independent of the selected coronal angle implant 20, may provide a desired sagittal angle β. Similar to FIG. 3, FIG. 4 shows various alternative sagittal angle implants 30a-c that may be used in lieu of sagittal angle implant 30 if different sagittal angles, β1, β2, or β3 are desired. Together, the sagittal angle implants 30, 30a-c may form part of a set 32 of sagittal angle implants that includes individual implants with different sagittal angles β. The set 32 may include individual implants that include different heights as well. As a non-limiting example, the set 32 may include a plurality of different implants, each including a different sagittal angle β varying from about −40 degrees to about +40 degrees. Furthermore, each sagittal angle implant 30, 30a-c may include a designator 34 to distinguish the individual implant 30, 30a-c from others in the set 32 as described above.

Figure 5:
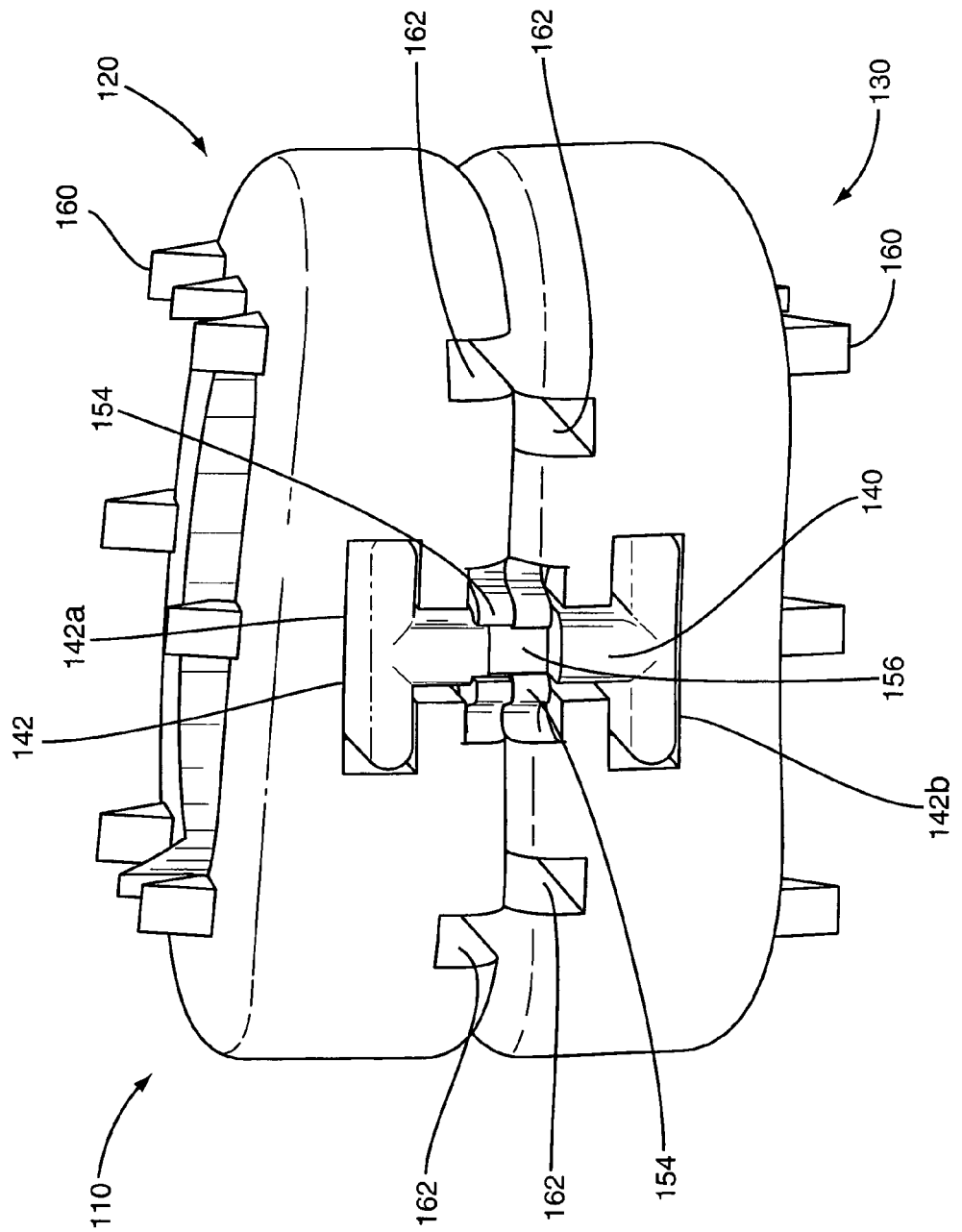
FIG. 5 is a perspective view of a vertebral implant according to one embodiment.
Figure 6:
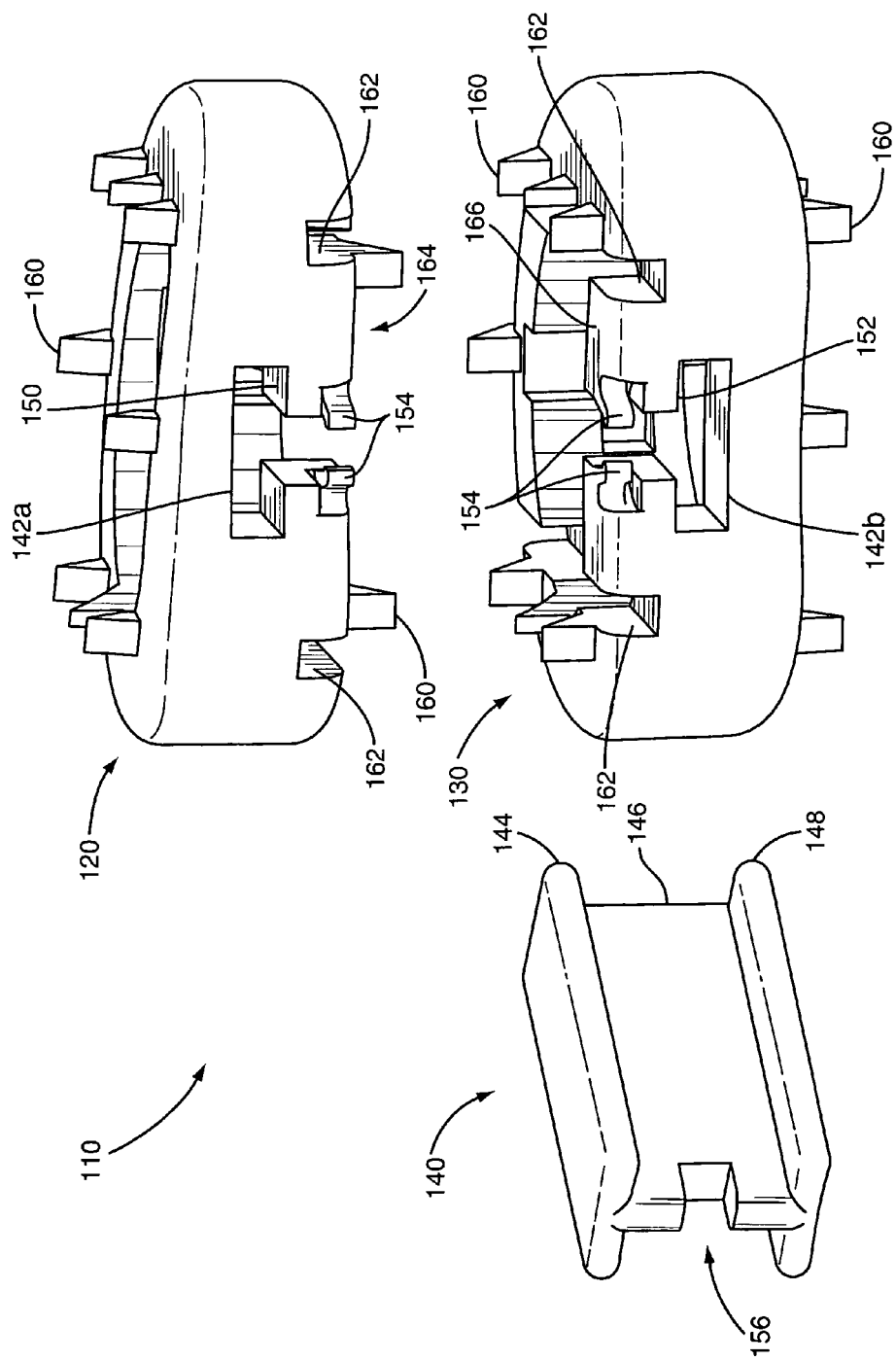
FIG. 6 is a perspective view depicting an exploded assembly of a vertebral implant according to one embodiment.

FIG. 5 depicts one embodiment of a vertebral implant 110 incorporating a coronal angle implant 120 and a sagittal angle implant 130 as described above. The embodiment shown in FIG. 5 also includes a connector 140 that holds the coronal angle implant 120 and the sagittal angle implant 130 together. FIG. 6 illustrates an exploded view of the vertebral implant 110 and more clearly shows various features of the coronal angle implant 120 and the sagittal angle implant 130.

The illustrated connector 140 includes an I-beam cross section and is sized to fit within a similarly shaped recess 142 that is formed in the coronal angle implant 120 and the sagittal angle implant 130. One portion 142a of the recess 142 is formed in the coronal angle implant 120 while the other portion 142b of the recess 142 is formed in the sagittal angle implant 130. In one embodiment, the recess 142 is symmetrically distributed within the coronal angle implant 120 and the sagittal angle implant 130. In one embodiment, a majority of the recess is disposed in one or the other of the coronal angle implant 120 and the sagittal angle implant 130. The connector 140 includes enlarged portions 144,148 disposed on opposite ends of a narrow intermediate portion 146. When the enlarged end portions 144, 148 are inserted into the corresponding portions 142a, 142b of the recess 142, contact between undercut surfaces 150,152 and the enlarged end portions 144, 148 prevents the coronal angle implant 120 and the sagittal angle implant 130 from separating. It should be understood that while an I-beam shape is portrayed for the connector 140, other shapes that include enlarged ends might be used to achieve the same effect. For example, the connector 140 may include shapes such as an hourglass or a dumbbell. The connector 140 may include other cross section shapes, including a C-shape, and S-shape, an X-shape, or other shape that sufficiently prevents separation of the coronal angle implant 120 and the sagittal angle implant 130. In other embodiments, retainer clips such as a C-clip, U-clip, or retainer ring may be used to hold the coronal angle implant 120 and sagittal angle implant 130 together.

The coronal angle implant 120 and the sagittal angle implant 130 also include retainers 154 that secure the connector 140 within the recess 142 in the coronal angle implant 120 and the sagittal angle implant 130. In the embodiment shown, the retainers 154 are implemented as pairs inwardly biased fingers that are spaced apart a distance that is less than the width of the intermediate portion 146 of the connector. The retainers 154 may be deflected away from each other to allow the connector 140 to fit into the recess 142. Once the connector 140 is inserted completely within the recess 142, the retainers 154 deflect to their normal position within a recess 156 in the connector 140. In the embodiment shown, the vertebral implant 110 includes a total of four retainers 154, with two each in the coronal angle implant 120 and the sagittal angle implant 130. In another embodiment, the coronal angle implant 120 and the sagittal angle implant 130 each include a single retainer 154. In another embodiment, a flexible retainer 154 may be disposed on the connector 140 and configured to engage a corresponding recess in the coronal angle implant 120 and the sagittal angle implant 130. Those skilled in the art will comprehend that other ways of securing the connector 140 in the coronal angle implant 120 and the sagittal angle implant 130 may be used.

The coronal angle implant 120 and the sagittal angle implant 130 also include a plurality of bone engagement features 160 disposed about the superior and inferior surfaces of each implant 120, 130. In the embodiment shown, these bone engagement features 160 are depicted as ramped teeth, though it should be understood that other types of features might be used. For example, the bone engagement features 160 may be implemented as pyramid shaped, diamond shaped, cone shaped, or other protruding feature adapted to engage, embed, scour, scrape, or decorticate the end plates of a vertebral body.

In conjunction with the bone engagement features 160, the coronal angle implant 120 and the sagittal angle implant 130 each include a plurality of recesses 162 disposed at the surface that contacts the other implant. Specifically, the coronal angle implant 120 includes these recesses 162 at the inferior surface 164. Similarly, the sagittal angle implant 130 includes recesses 162 at the superior surface 166. In embodiments where the relative position of the coronal angle implant 120 and the sagittal angle implant 130 are reversed, the recesses 162 may be disposed at the opposite surface (i.e., the surface that is positioned in contact with the other implant 120, 130). In other embodiments, the recesses 162 are disposed on both superior and inferior surfaces of the implant 120, 130.

The recesses 162 on the coronal angle implant 120 are substantially aligned with the bone engagement features 160 of the sagittal angle implant 130. Conversely, the recesses 162 on the sagittal angle implant 130 are substantially aligned with the bone engagement features 160 of the coronal angle implant 120. With this configuration, the coronal angle implant 120 and the sagittal angle implant 130 are able to be positioned with the inferior surface 164 of the coronal angle implant 120 in contact with the superior surface 166 of the sagittal angle implant 130.

Furthermore, since the bone engagement features 160 are disposed about the superior and inferior surfaces of each implant 120,130, each implant 120,130 may be surgically installed without the other. Thus, for example, if a particular patient requires coronal angle correction, a coronal angle implant 120 that includes the appropriate coronal angle α may be inserted between vertebral bodies in the appropriate region of the spine. Similarly, if a particular patient requires sagittal angle correction, a sagittal angle implant 130 with the appropriate sagittal angle β may be inserted between vertebral bodies in the appropriate region of the spine. If a particular patient requires a multiplanar correction, a coronal angle implant 120 with an appropriate coronal angle α and a sagittal angle implant 130 with an appropriate sagittal angle β may be used together and inserted between vertebral bodies in the appropriate region of the spine. Accordingly, each of the coronal angle implant 120 and the sagittal angle implant 130 may be used either in conjunction with the other implant, or by itself.

Figure 7:
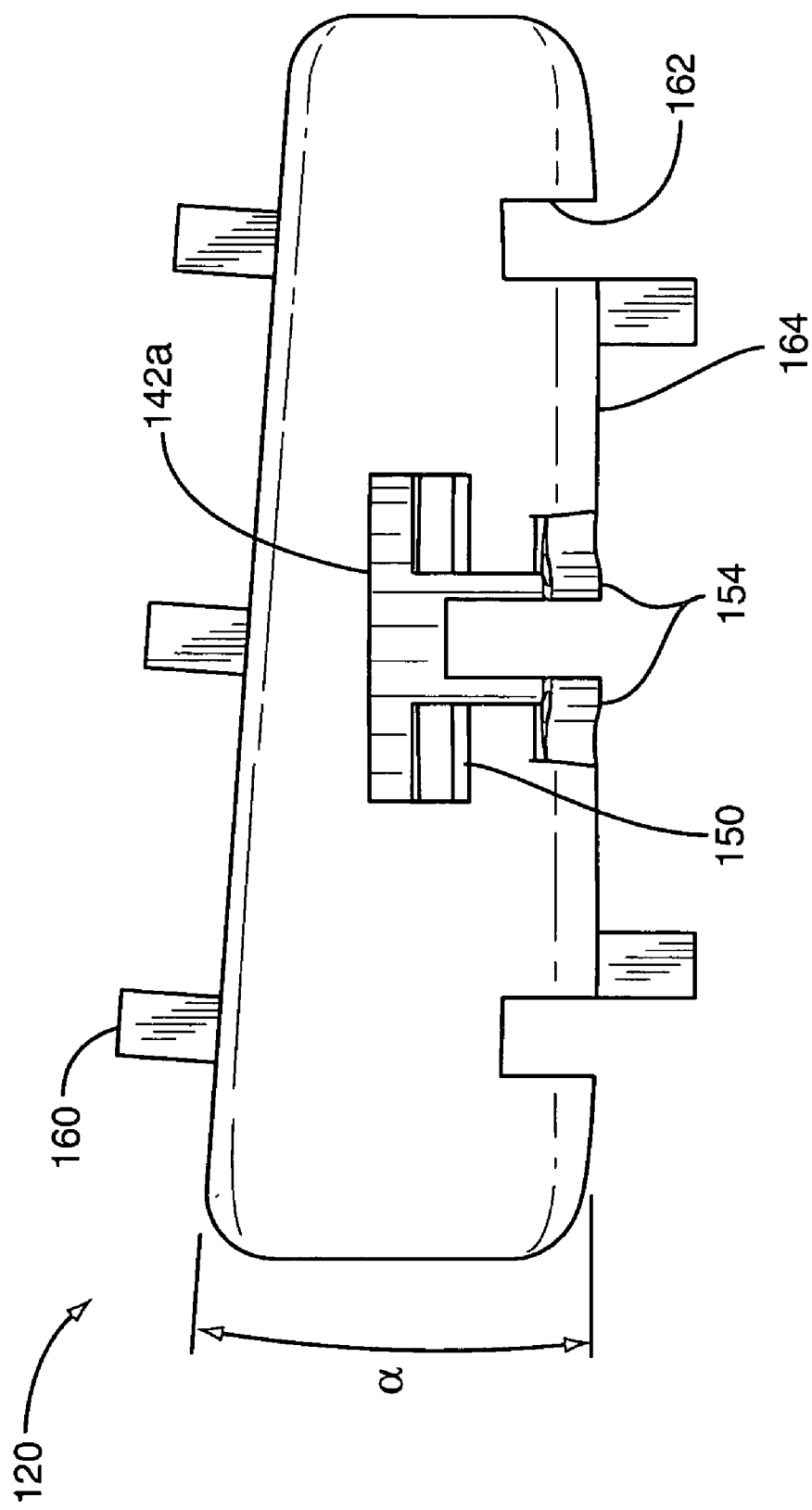
FIG. 7 is an anterior view of a coronal angle implant according to one embodiment.
Figure 8:
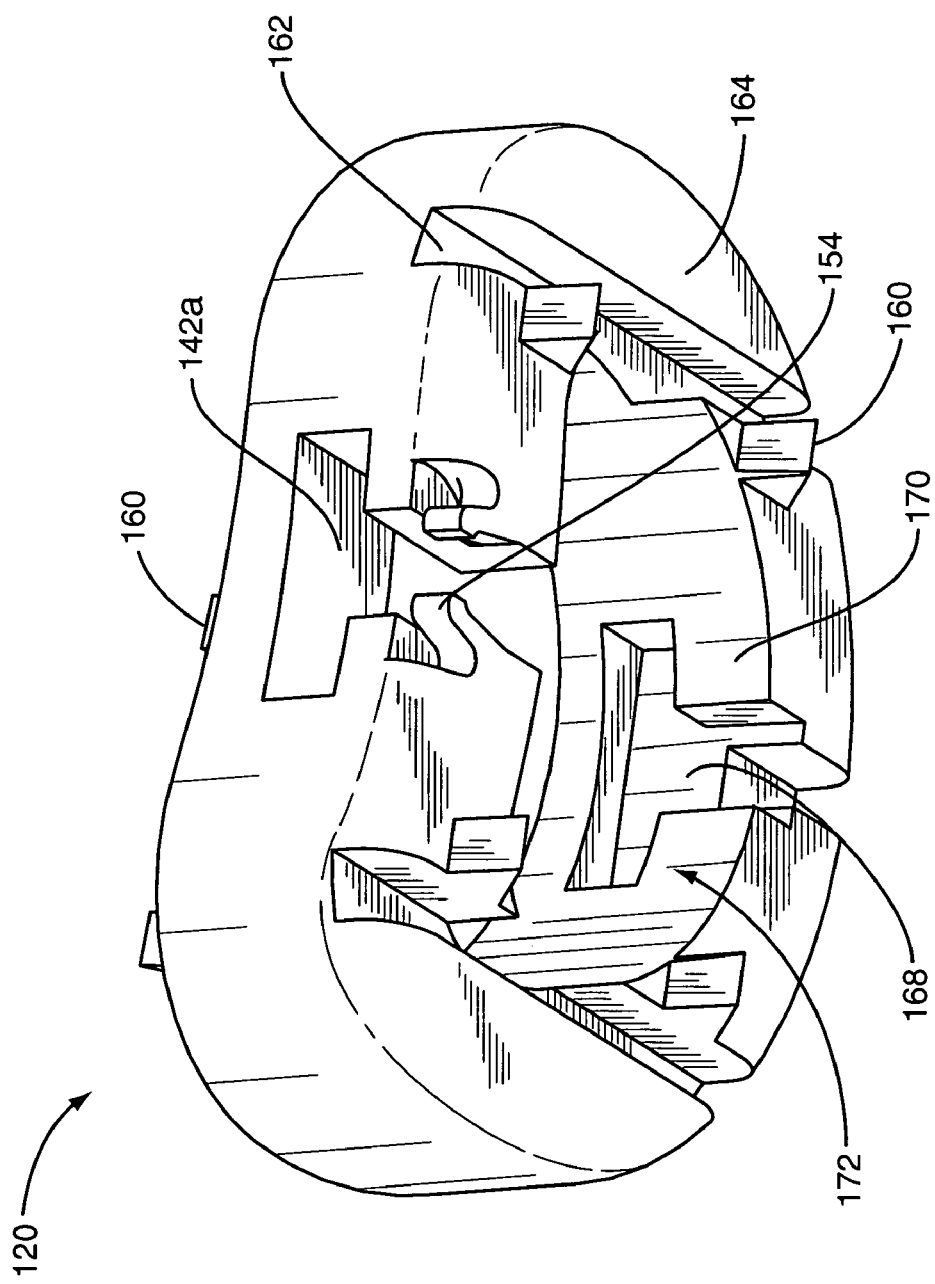
FIG. 8 is a perspective view of a coronal angle implant according to one embodiment.
Figure 9:
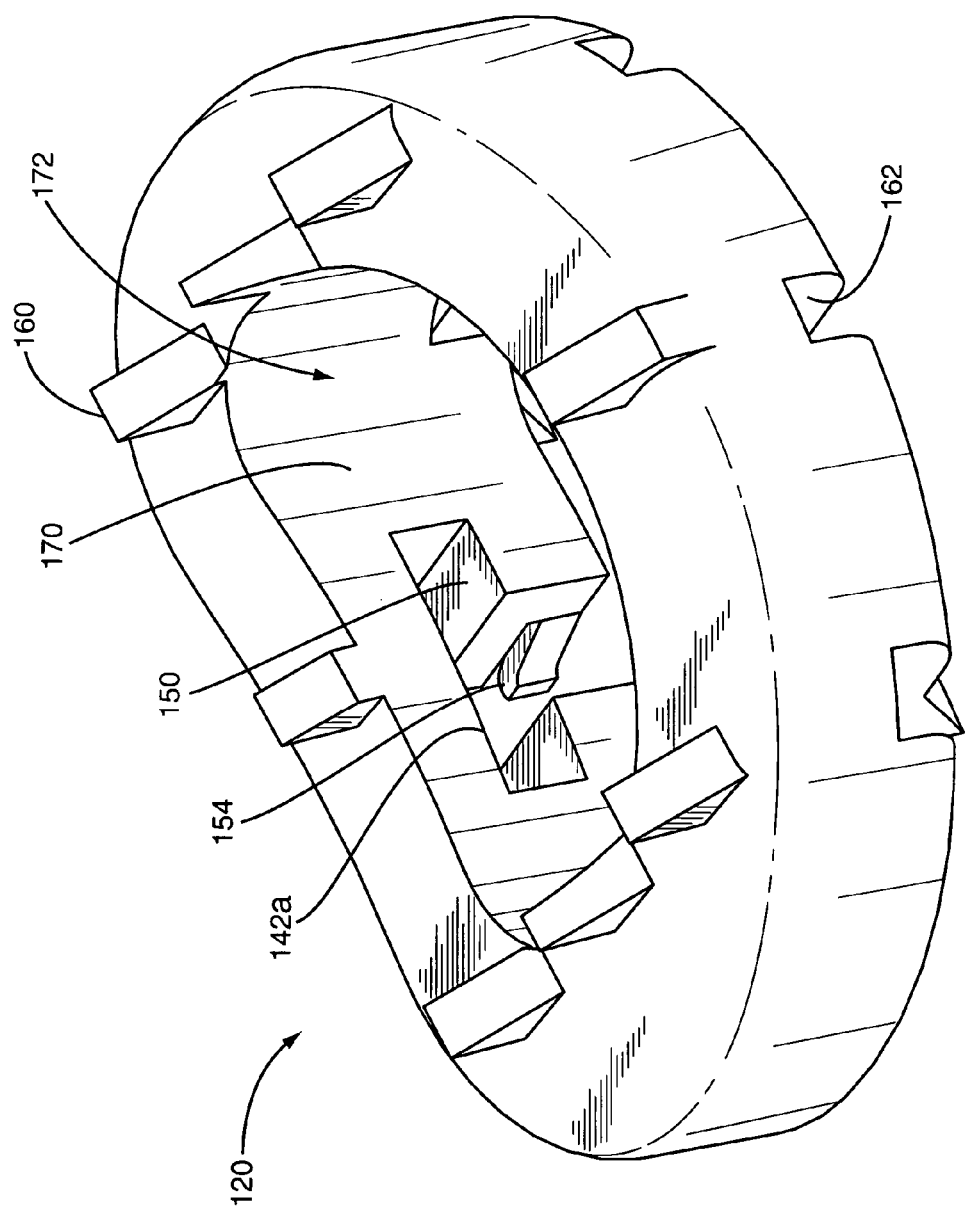
FIG. 9 is a perspective view of a coronal angle implant according to one embodiment.

FIGS. 7, 8, and 9 depict various views of the exemplary coronal angle implant 120. FIG. 7 shows a posterior view of the coronal angle implant 120 and illustrates the coronal angle α. FIG. 8 shows a perspective view of the coronal angle implant 120 depicted from inferior and posterior directions. The inferior surface 164 of the coronal angle implant 120 is more clearly visible in FIG. 8. Further, FIG. 8 shows that the coronal angle implant 120 includes an inner wall 170 that defines an inner cavity 172. Further, the recess 142a for connector 140 extends across the cavity 172 but ends at a stop surface 168. That is, the recess 142a does not extend all the way through the coronal angle implant 120. Thus, an inserted connector 140 is constrained within the recess 142a by the stop surface 168 and the retainers 154.

Figure 12:
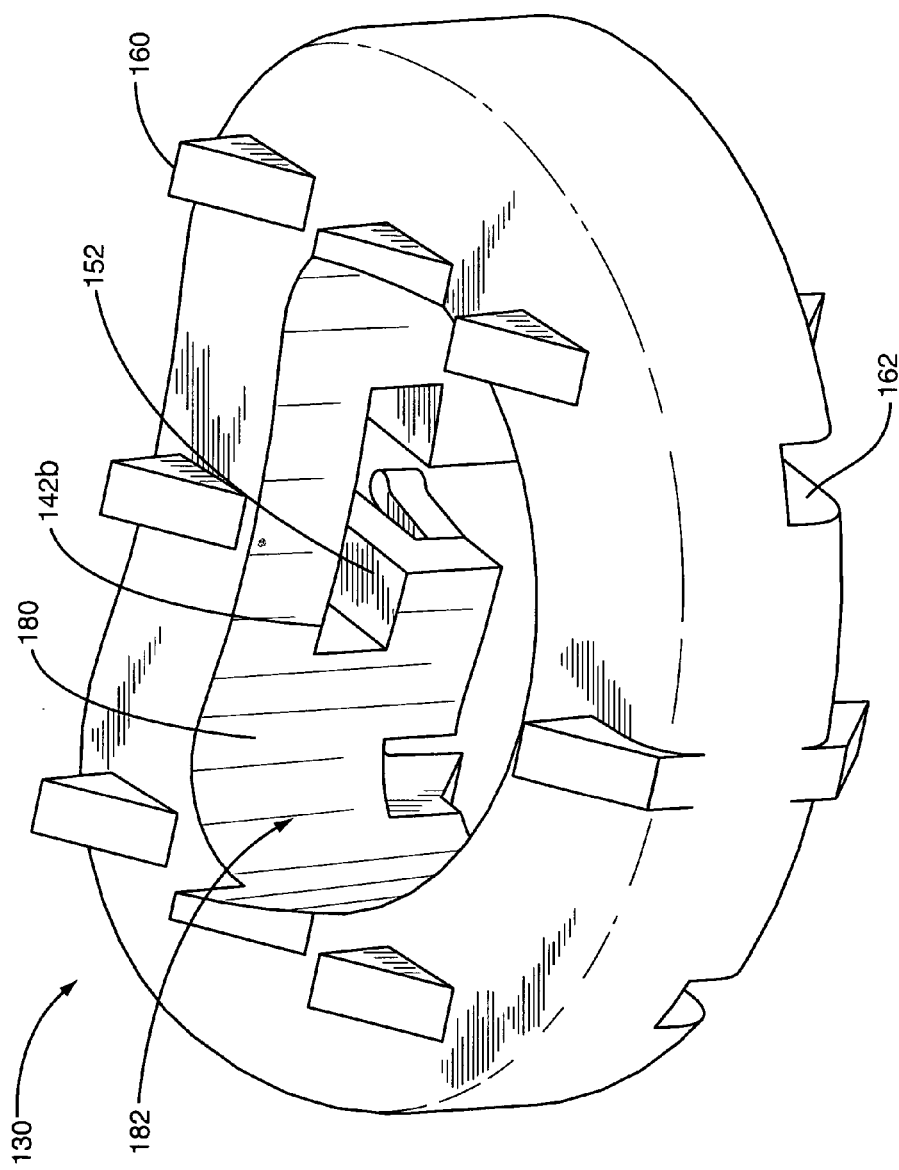
FIG. 12 is a perspective view of a sagittal angle implant according to one embodiment.

FIG. 9 shows a perspective view of the coronal angle implant 120 depicted from superior and anterior directions. The inner wall 170 and inner cavity 172 are clearly visible in this particular view. FIG. 12 shows that a similar cavity 182 exists in the sagittal angle implant 130. Notably, the connector 140 is exposed within these cavities 172, 182. As a result, the connector 140 may be constructed with a bone growth promoting material such as BMP, DBM, hydroxyapatite, allograft, autograft or other osteoinductive growth factors to facilitate fusion between vertebral bodies and the implant 10. These and other types of bone growth promoting materials may be packed into the cavities 172, 182 around the connector 140 to further promote fusion between the implant 110 and vertebral bodies.

Figure 10:
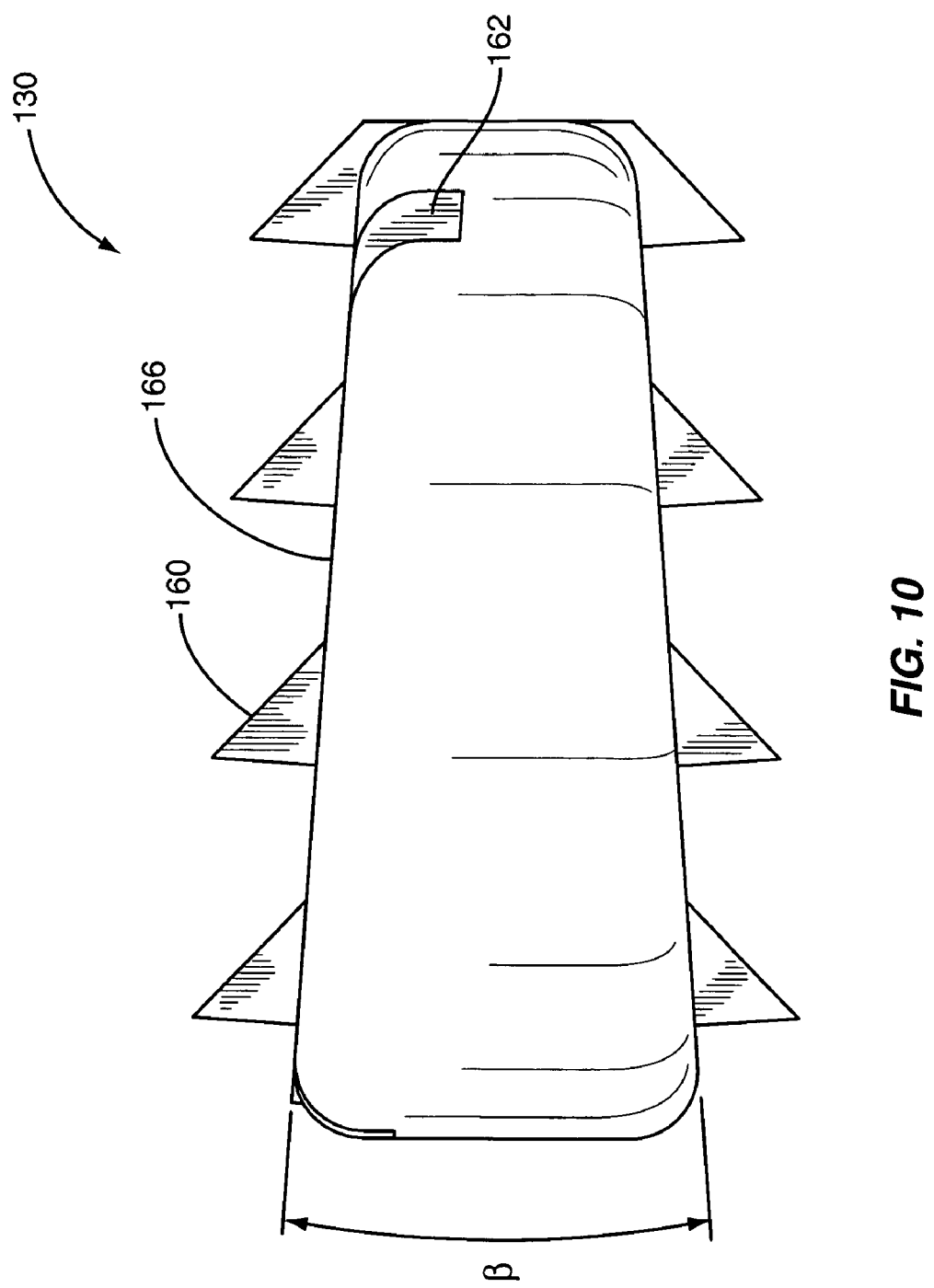
FIG. 10 is a lateral view of a sagittal angle implant according to one embodiment.
Figure 11:
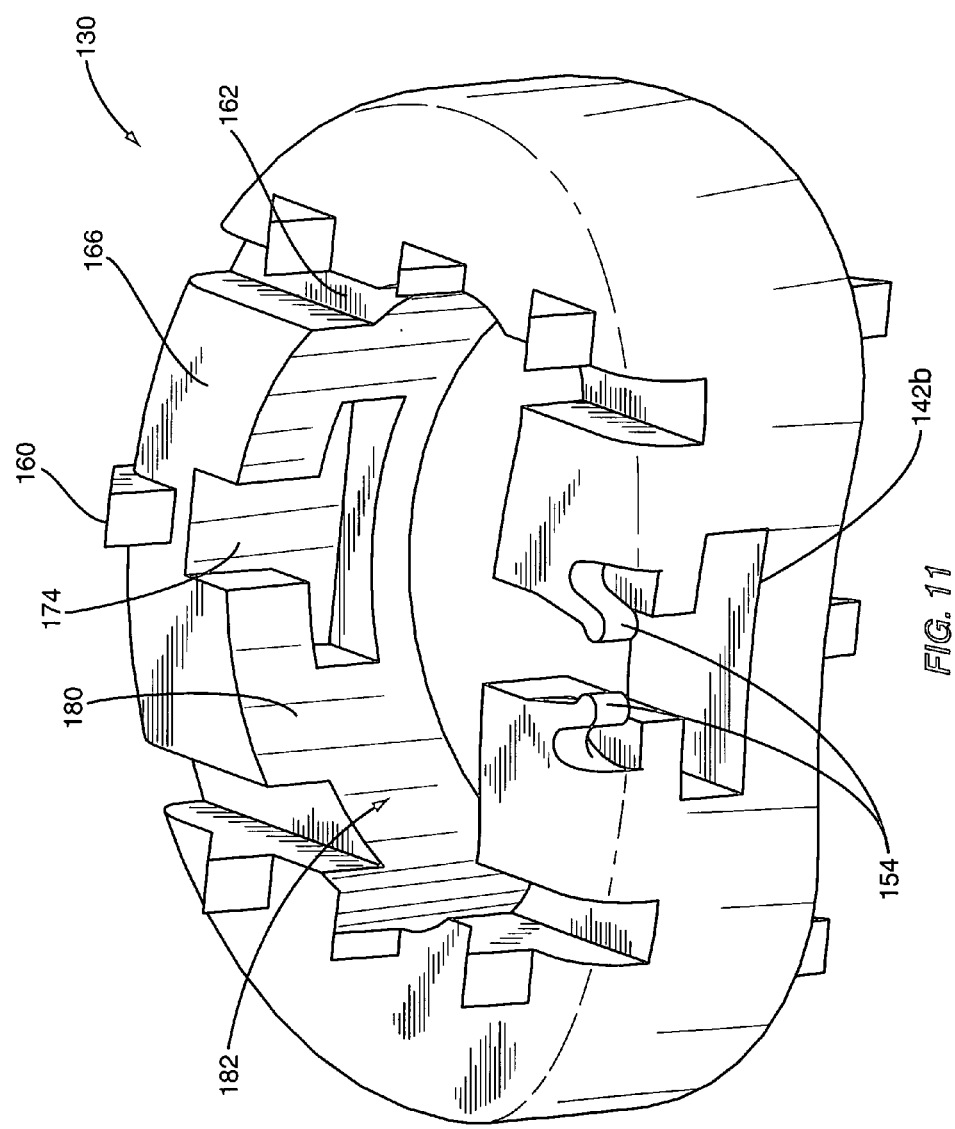
FIG. 11 is a perspective view of a sagittal angle implant according to one embodiment.

FIGS. 10, 11, and 12 depict various views of the exemplary sagittal angle implant 130. FIG. 10 shows a lateral view of the sagittal angle implant 130 and illustrates the sagittal angle β. FIG. 11 shows a perspective view of the sagittal angle implant 130 depicted from superior and posterior directions. FIG. 11 shows that the sagittal angle implant 130 includes an inner wall 180 that defines an inner cavity 182 similar to the cavity 172 in the coronal angle implant 120. Furthermore, FIG. 11 shows that the recess 142b for connector 140 extends across the cavity 182 but ends at a stop surface 174. That is, the recess 142a does not extend all the way through the sagittal angle implant 130. Similar to the coronal angle implant 120 configuration, an inserted connector 140 is constrained within the recess 142b by the stop surface 174 and the retainers 154. FIG. 12 shows a perspective view of the sagittal angle implant 130 depicted from inferior and anterior directions. The inner wall 180 and inner cavity 182 are clearly visible in this particular view.

Figure 13:
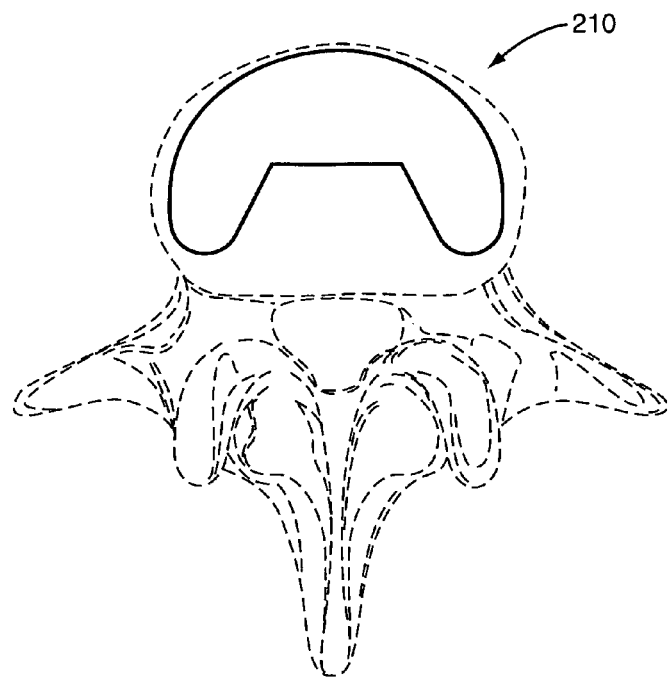
FIG. 13 is a top view of a vertebral implant according to one embodiment shown relative to a vertebral body.
Figure 14:
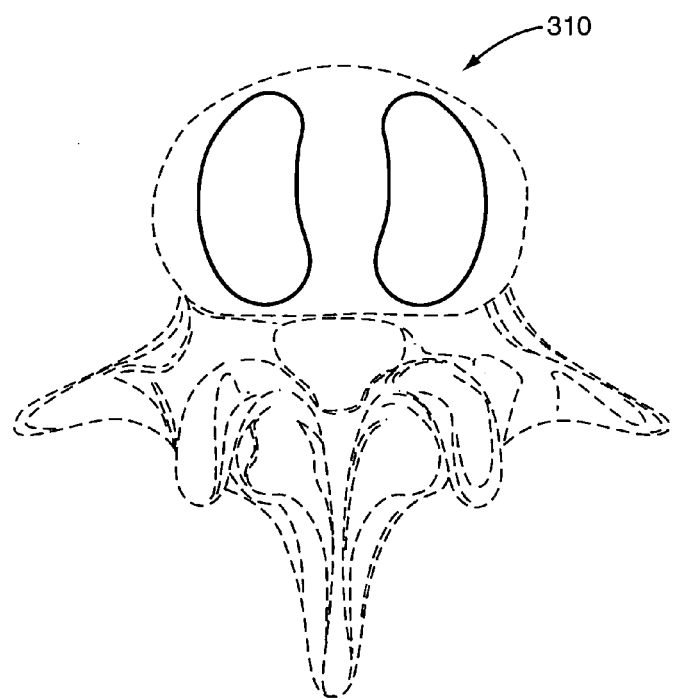
FIG. 14 is a top view of a vertebral implant according to one embodiment shown relative to a vertebral body.

The vertebral implants 10, 110, 120, 130 disclosed above generally include a kidney shape, though other shapes and contours may be used. In further embodiments, the vertebral implant may take on other types of configurations, such as, for example, a circular shape, semi-oval shape, bean-shape, D-shape, elliptical-shape, egg-shape, or any other shape that would occur to one of skill in the art. The vertebral implant could also be described as being annular, U-shaped, C-shaped, V-shaped, horseshoe-shaped, semi-circular shaped, semi-oval shaped, or other similar terms defining an implant including at least a partially open or hollow construction. For example, FIG. 13 shows one embodiment of a vertebral implant 210 that includes a horseshoe configuration. The implant 210 may be implanted from an anterior, lateral, or posterior approach. In other embodiments, the vertebral implant may take on substantially solid configurations, such as, for example, block-like or plate-like configurations that do not define an open inner region. The embodiments shown in FIGS. 1-4 provide one example of a substantially solid configuration. Other embodiments may include an annular configuration similar to the embodiments illustrated in FIGS. 5-12. Other embodiments may include multiple, unattached portions, such as TLIF or PLIF cages or the exemplary implant 310 shown in FIG. 14.

Figure 15:
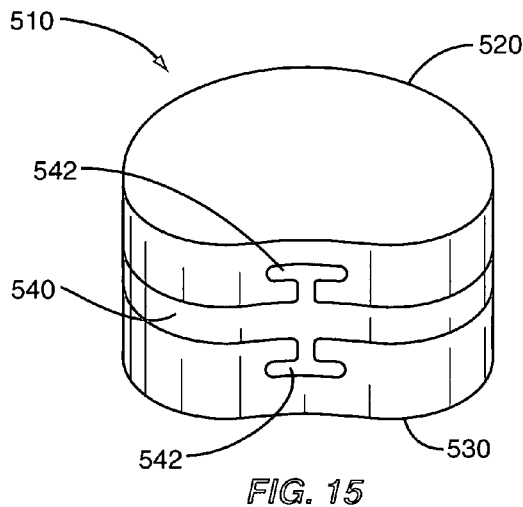
FIG. 15 is a perspective view of a vertebral implant according to one embodiment.
Figure 16:
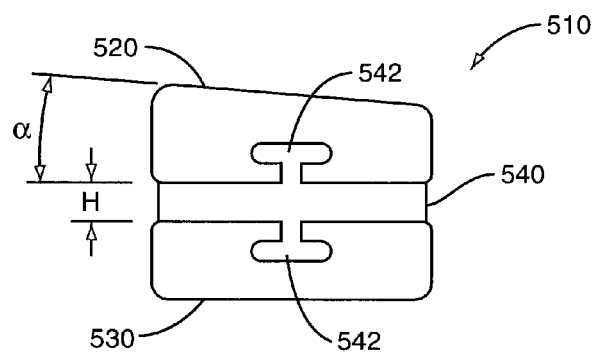
FIG. 16 is an anterior view of a vertebral implant according to one embodiment.
Figure 17:
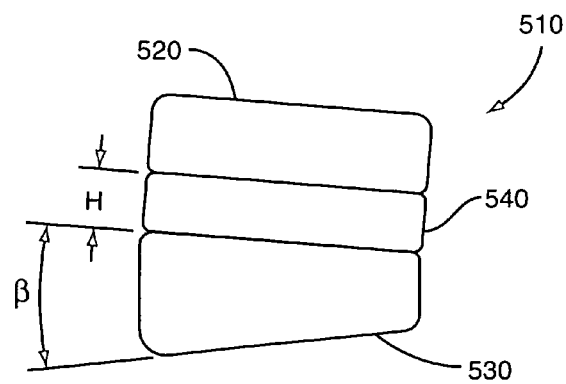
FIG. 17 is a lateral view of a vertebral implant according to one embodiment.

As discussed above, the vertebral implants disclosed herein may be used in disc replacement or vertebral replacement surgeries. FIGS. 15, 16, and 17 show an embodiment 510 of a vertebral implant that includes a spacer 540 that serves at least two purposes. First, the spacer 540 includes enlarged portions 542 to retain the coronal angle implant 520 and the sagittal angle implant 530. Thus, the spacer 540 is similar to the connector 140 in this regard. Second, the spacer 540 adds additional height H to the vertebral implant 510 that may be necessary for vertebrectomy and corpectomy procedures. Consistent with previous embodiments, the coronal angle implant 520 includes an associated coronal angle α for spinal correction in the coronal plane. Similarly, the sagittal angle implant 530 includes an associated sagittal angle β for spinal correction in the sagittal plane. The coronal angle implant 520 is shown in a superior position relative to the spacer 540 and sagittal angle implant 530. In other embodiments, the sagittal angle implant 530 may be disposed superior to the spacer 540 and coronal angle implant 520.

Embodiments disclosed above have not included any particular surface geometry, coating, or porosity as are found in conventionally known vertebral implants. Surface features such as these are used to promote bone growth and adhesion at the interface between an implant and a vertebral body. Examples of features used for this purpose include, for example, teeth, scales, keels, knurls, and roughened surfaces. Some of these features may be applied through post-processing techniques such as blasting, chemical etching, and coating, such as with hydroxyapatite. The superior and inferior bone interface surfaces of the vertebral implant may also include growth-promoting additives such as bone morphogenetic proteins. Alternatively, pores, cavities, or other recesses into which bone may grow may be incorporated via a molding process. Other types of coatings or surface preparation may be used to improve bone growth into or through the bone-contact surfaces.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For instance, the geometries described herein may be implemented in ALIF, PLIF, or TLIF cages with an interior cavity for inserting bone growth promoting materials. The present embodiments are, therefore, to be considered in all respects as illustrative and not restrictive, and all changes coming within the meaning and equivalency range of the appended claims are intended to be embraced therein.

What is claimed is:

1. An intervertebral implant for insertion into a patient between vertebral bodies comprising:
    a first body including an inferior surface, a superior surface, and a first exterior perimeter surface extending transverse to and connecting the inferior and superior surfaces, the first body including a rigid tapered shape with a height of the first body measured between the inferior and superior surfaces gradually increasing from one end of the first body to an opposing end of the first body, the inferior and superior surfaces of the first body forming a fixed first angle that is aligned in a first direction, the first body having a first recess formed therein and opening to the first perimeter surface;
    a second body including an inferior surface, a superior surface, and a second exterior perimeter surface extending transverse to and connecting the inferior and superior surfaces, the second body including a rigid tapered shape with a height of the second body measured between the inferior and superior surfaces gradually increasing from one end of the second body to an opposing end of the second body, the inferior and superior surfaces of the second body forming a fixed second angle that is aligned in a second direction, the second body having a second recess formed therein and opening to the second perimeter surface;
    a single connector comprising a first end, a second end and a narrow intermediate portion, the connector including enlarged portions disposed at the first end and the second end, the connector extending in the first and second recesses to couple the first and second bodies together, the connector positioned along a central plane that extends through the superior and inferior surfaces of each of the first and second bodies, wherein the engagement of the enlarged portions with the recesses prevents the first and second bodies from separating; and
    each of the first and second bodies include a pair of inwardly facing retainers that are spaced apart a distance that is less then a width of the narrow intermediate portion such that the narrow intermediate portion is secured within the retainers to prevent the connector from dislodging from the first and second bodies,
    wherein the first and second bodies are stackable into a stacked configuration such that the first and second directions are orthogonal to one another and wherein in the stacked configuration, the interior surface of the first body engages the superior surface of the second body.

2. The intervertebral implant of claim 1 further comprising a retainer disposed on at least one of the first and second bodies; the retainer configured to secure the connector to the first and second bodies.

3. The intervertebral implant of claim 1 wherein the connector comprises a spacer configured to be disposed between the first and second bodies to establish a desired spacing between the superior surface of the first body and the inferior surface of the second body.

4. An intervertebral implant for insertion into a patient between vertebral bodies comprising:
    a coronal angle implant including an inferior surface, a superior surface, and a first exterior perimeter surface extending transverse to and connecting the inferior and superior surfaces, the coronal angle implant including a tapered shape that tapers from one end to an opposing end with the inferior and superior surfaces of the coronal angle implant forming a coronal angle correction and being fixed relative to each other, the coronal angle implant having a first recess formed therein and opening to the first perimeter surface;
    a sagittal angle implant including an inferior surface, a superior surface, and a second exterior perimeter surface extending transverse to and connecting the inferior and superior surfaces, the sagittal angle implant including a tapered shape that tapers from one end to an opposing end with the inferior and superior surfaces of the sagittal angle implant forming a sagittal angle correction and being fixed relative to each other, the sagittal angle implant having a second recess formed therein and opening to the second perimeter surface;

a single connector comprising a first end, a second end and a narrow intermediate portion, the connector including enlarged portions disposed at the first end and the second end, the connector disposed in the first and second recesses centered on the implants to permanently couple the coronal angle and sagittal angle implants together, wherein the engagement of the enlarged portions with the recesses prevents the coronal angle and sagittal angle implants from separating; and each of the coronal angle and sagittal angle implants include a pair of inwardly facing retainers that are spaced apart a distance that is less then a width of the narrow intermediate portion such that the narrow intermediate portion is secured within the retainers to prevent the connector from dislodging from the coronal angle and sagittal angle implants, wherein the inferior surface of one of the coronal angle implant and sagittal angle implant engages the superior surface of the other of the coronal angle implant and sagittal angle implant to fixedly position the implants relative to one another.

5. The intervertebral implant of claim 4 wherein the coronal angle and sagittal angle implants are stackable into a stacked configuration such that the coronal angle correction and the sagittal angle correction are substantially perpendicular to each other.

6. The intervertebral implant of claim 4 wherein the coronal angle implant and the sagittal angle implant comprise bone engagement protrusions extending from their respective inferior and superior surfaces.

7. An intervertebral implant for insertion into a patient between vertebral bodies comprising:
   a first wedge-shaped body including:
      a first angle formed between a first inferior surface and a first superior surface; a first bone engagement protrusion extending outward from the first inferior surface;
      a first exterior perimeter surface extending transverse to and connecting the first inferior surface and the first superior surface;
      a first recess opening to the first perimeter surface;
   a second wedge-shaped body including:
      a second angle formed between a second inferior surface and a second superior surface;
      a second exterior perimeter surface extending transverse to and connecting the second inferior surface and the second superior surface;
      a second recess opening to the second perimeter surface;
      a third recess formed in the second superior surface;
   a single connector comprising a first end, a second end and a narrow intermediate portion, the connector including enlarged portions disposed at the first end and the second end, the connector disposed in the first and second recesses to couple the first and second wedge-shaped bodies together, the connector positioned along a central plane of the implant that extends through the superior and inferior surfaces of each of the first and second bodies, wherein the engagement of the enlarged portions with the recesses prevent the first and second wedge shaped bodies from separating; and
   each of first and second wedge shaped bodies include a pair of inwardly facing retainers that are spaced apart a distance that is less then a width of the narrow intermediate portion such that the narrow intermediate portion is secured within the retainers to prevent the connector from dislodging from the first and second wedge shaped bodies,
   the first and second bodies stacked in a rigid construction for insertion between the vertebral bodies with:
   the first and second angles respectively oriented in first and second different planes;
   the third recess receiving the first bone engagement protrusion; and
   the first inferior surface and the second superior surface being in contact.

8. The intervertebral implant of claim 7 wherein the first body includes a fourth recess in the first inferior surface, the second body includes a
   second bone engagement protrusion in the second superior surface, the fourth recess positioned to accept the second bone engagement protrusion.

9. The intervertebral implant of claim 7 wherein the first body includes a third bone engagement protrusion in the first superior surface, the second body includes a fourth bone engagement protrusion in the second inferior surface, the third and fourth bone engagement protrusions configured to engage the vertebral bodies.

10. The intervertebral implant of claim 7 wherein the first angle is oriented in a first plane and the second angle is oriented in a second plane different from the first plane.

* * * * *